(12) United States Patent
Arbab et al.

(10) Patent No.: US 9,261,456 B2
(45) Date of Patent: Feb. 16, 2016

(54) TERAHERTZ SPECTROSCOPY OF ROUGH SURFACE TARGETS

(75) Inventors: Mohammad Hassan Arbab, Seattle, WA (US); Dale P. Winebrenner, Seattle, WA (US); Antao Chen, Lake Forest Park, WA (US); Eric I. Thorsos, Woddinville, WA (US)

(73) Assignee: University of Washington through its Center for Commercialization, Seattle, WA (US)

( * ) Notice: Subject to any disclaimer, the term of this patent is extended or adjusted under 35 U.S.C. 154(b) by 740 days.

(21) Appl. No.: 13/358,437

(22) Filed: Jan. 25, 2012

(65) Prior Publication Data

US 2012/0191371 A1    Jul. 26, 2012

Related U.S. Application Data

(60) Provisional application No. 61/435,871, filed on Jan. 25, 2011.

(51) Int. Cl.
*G01N 21/3586* (2014.01)

(52) U.S. Cl.
CPC ...... *G01N 21/3586* (2013.01); *G01N 2201/129* (2013.01)

(58) Field of Classification Search
CPC .................................................. G01N 21/3586
USPC .......................................................... 702/28
See application file for complete search history.

(56) References Cited

U.S. PATENT DOCUMENTS

| | | | |
|---|---|---|---|
| 5,623,145 A | 4/1997 | Nuss | |
| 5,710,430 A | 1/1998 | Nuss | |
| 5,894,125 A | 4/1999 | Brener | |
| 5,939,721 A | 8/1999 | Jacobsen | |
| 6,078,047 A * | 6/2000 | Mittleman et al. | 250/338.1 |
| 7,221,451 B2 | 5/2007 | Ohtake | |
| 7,728,296 B2 | 6/2010 | Cole | |
| 7,781,736 B2 | 8/2010 | Logan, Jr. | |
| 7,804,069 B2 | 9/2010 | Tribe | |
| 2007/0235650 A1 * | 10/2007 | Federici et al. | 250/341.8 |
| 2009/0206263 A1 * | 8/2009 | Rahman | 250/341.1 |

OTHER PUBLICATIONS

Wu et al., "On the trend, detrending, and variability of nonlinear and nonstationary time series", (2007), PNAS Sep. 18, 2007, vol. 104, No. 38 14889-14894.*
Mittleman et al., "Gas sensing using terahertz time-domain spectroscopy", 1998, Appl. Phys. B 67, 379-390.*
Ortolani et al., "Surface roughness effects on the terahertz reflectance of pure explosive materials", (2008), Applied Physics Letters 93, 081906.*

(Continued)

*Primary Examiner* — Regis Betsch
(74) *Attorney, Agent, or Firm* — Christensen O'Connor Johnson Kindness PLLC (57) ABSTRACT

A method and system for analyzing noisy terahertz spectroscopy data transforms the measured time-dependent data into frequency space, for example, using a discrete Fourier transform, and then transforms the frequency spectrum into wavelet frequency space. The twice-transformed data is analyzed to identify spectroscopic features of the signal, for example, to identify a resonance frequency. The method may be used, for example, in a stand-off detector to identify particular chemicals in a target.

19 Claims, 6 Drawing Sheets

(56) References Cited

OTHER PUBLICATIONS

Cheng Te et al., "Investigation of biomaterial classification using T-rays", (2002), Proceedings of SPIE vol. 4937, 294-306.*

Tielrooij et al., "Dielectric Relaxation Dynamics of Water in Model Membranes Probed by Terahertz Spectroscopy", (2009), Biophysical Journal vol. 97 Nov. 2009 2484-2492.*

Rinnan et al., "Review of the most common pre-processing techniques for near-infrared spectra", 2009, Trends in Analytical Chemistry vol. 28, No. 10 p. 1201-1222.*

Ahmed Zayed, "Pointwise Convergence of a Class of Non-Orthogonal Wavelet Expansions", 2000, Proceeedings of the American Mathematical Society, vol. 128, No. 12 pp. 3629-3637.*

Definitions from http://Dictionary.com Apr. 19, 2015.*

Bos et al., "The wavelet transform for pre-processing IR spectra in the identification of mono- and di-substituted benzenes", 1994, Chemometrics and Intelligent Laboratory Systems 23 (1994) 115-122.*

Chen et al., "Frequency-wavelet domain deconvolution for terahertz reflection imaging and spectroscopy", 2010 / vol. 18, No. 2 / Optics Express pp. 1177-1190.*

Ferguson et al., "De-Noising techniques for teraherz responses of biological samples", 2001, Microelectronics Journal 32, pp. 943-953.*

Arbab, M.N., et al., "Retrieval of Terahertz Spectroscopic Signatures in the Presence of Rough Surface Scattering Using Wavelet Methods," Applied Physics Letters 97:181903-1-181903-3, Nov. 1, 2010.

Ortolani, M., et al., "Surface Roughness Effects on the Terahertz Reflectance of Pure Explosive Materials," Applied Physics Letters 93:081906-1-081906-3, Aug. 25, 2008.

Tribe, W.R., et al., "Hidden Object Detection: Security Applications of Terahertz Technology," in R.J. Hwu (ed.), "Terahertz and Gigahertz Electronics and Photonics III," Proceedings of SPIE 5354:168-176, Apr. 2004.

Yamamoto, K., et al., "Noninvasive Inspection of C-4 Explosive in Mails by Terahertz Time-Domain Spectroscopy," Japan Society of Applied Physics 43(3B):L414-L417, Mar. 2004.

Zurk, L.M., et al., "Terahertz Scattering From Granular Material," Journal of the Optical Society of America B 24(9): 2238-2243, Sep. 2007.

Allis, D.G., et al., "Assignment of the Lowest-Lying THz Absorption Signatures in Biotin and Lactose Monohydrate by Solid-State Density Functional Theory," Chemical Physics Letters 440(4-6):203-209, Jun. 2007.

Arbab, M.H., et al., "Effect of Surface Scattering on Terahertz Time Domain Spectroscopy of Chemicals," Proceedings of SPIE 6893, Terahertz Technology and Applications, pp. 68930C-1-68930C-8, Feb. 2008.

Brown, E.R., et al., "On the Strong and Narrow Absorption Signature in Lactose at 0.53 THz," Applied Physics Letters 90(6):061908-1-061908-3, Feb. 2007.

Daubechies, I., "Orthonormal Bases of Compactly Supported Wavelets. II. Variations on a Theme," SIAM Journal of Mathematical Analysis 24(2):499-519, Mar. 1993.

Dikmelik, Y., et al., "Effects of Surface Roughness on Reflection Spectra Obtained by Terahertz Time-Domain Spectroscopy," Optics Letters 31(24):3653-3655, Dec. 2006.

Donoho, D.L., "De-Noising by Soft-Thresholding," IEEE Transactions on Information Theory 41(3):613-627, May 1995.

Ferguson, B., and X.-C. Zhang, "Materials for Terahertz Science and Technology," Nature Materials 1(1):26-33, Sep. 2002.

Ferguson, B., and D. Abbott, "Wavelet De-Noising of Optical Terahertz Pulse Imaging Data," Fluctuation and Noise Letters 1(2):L65-L69, Jun. 2001.

Gómez González, J.F., "Wavelet Methods for Time Series Analysis: Curso: Análisis De Sistemas Dinámicos No Lineales: Aplicación a Los Sistemas Naturales," course presentation, Universidad de La Laguna, Canary Islands, n.d., 45 pages.

Handley, J.W., et al., "Wavelet Compression in Medical Terahertz Pulsed Imaging," Physics in Medicine and Biology 47(21):3885-3892, Nov. 2002.

Kemp, M.C., "Security Applications of Terahertz Technology," Proceedings of SPIE 5070, Terahertz for Military and Security Applications, pp. 44-52, Aug. 2003.

Leahy-Hoppa, M.R., et al., "Terahertz Spectroscopy Techniques for Explosives Detection," Analytical and Bioanalytical Chemistry 395(2):247-257, Sep. 2009.

Liu, H.-B., et al., "Detection and Identification of Explosive RDX by THz Diffuse Reflection Spectroscopy," Optics Express 14(1):415-423, Jan. 2006.

Pedersen, P.C., and A. Grebe, "Application of Time Delay Spectrometry for Rough Surface Characterization," Ultrasonics 39(2):101-108, Mar. 2001.

Shen, Y.C., et al., "Detection and Identification of Explosives Using Terahertz Pulsed Spectroscopic Imaging," Applied Physics Letters 86(24):241116-1-241116-3, Jun. 2005.

Shen, Y.C., et al., "Elimination of Scattering Effects in Spectral Measurement of Granulated Materials Using Terahertz Pulsed Spectroscopy," Applied Physics Letters 92(5):051103-1-051103-3, Feb. 2008.

Tonouchi, M., "Cutting-Edge Terahertz Technology," Nature Photonics 1(2):97-105, Feb. 2007.

Winebrenner, D.P., et al., "Mapping Greenland Accumulation Rates Using Observations of Thermal Emission at 4.5-cm Wavelength," Journal of Geophysical Research 106(D24):33,919-33,934, Dec. 2001.

Zurk, L.M., et al., "Electromagnetic Scattering Calculations for Terahertz Sensing," Proceedings of SPIE 6472, Terahertz and Gigahertz Electronics and Photonics VI, pp. 6472A-1-6472A-9, Feb. 2007.

Zurk, L.M., et al., "Scattering Effects in Terahertz Reflection Spectroscopy," Proceedings of SPIE 6949, Terahertz and Gigahertz Electronics and Photonics VI, pp. 694907-1-694909-8, Apr. 2008.

* cited by examiner

TERAHERTZ SPECTROSCOPY OF ROUGH SURFACE TARGETS

CROSS-REFERENCE TO RELATED APPLICATION

This application claims the benefit of Provisional Application No. 61/435,871, filed Jan. 25, 2011, the entire disclosure of which is hereby incorporated by reference herein.

STATEMENT OF GOVERNMENT LICENSE RIGHTS

This invention was made with Government support under grant number N00014-05-1-0843 awarded by Office of Naval Research. The Government has certain rights in the invention.

BACKGROUND

Recent developments in methods for generating and detecting terahertz radiation have produced an interest in using terahertz frequency spectrum data for detecting the presence of chemicals relatively unobtrusively. For example, certain chemicals can be identified by the frequency of their absorption spectrum resonance in the terahertz range using Terahertz Time-Domain Spectroscopy (THz-TDS). Typically, in THz-TDS a sequence of femtosecond pulses from a mode-locked laser are focused onto a semiconductor that is configured to produce THz radiation. Early methods and apparatus for terahertz imaging are described in U.S. Pat. No. 5,623,145, to Nuss, and in U.S. Pat. No. 5,710,145, to Nuss, both of which are hereby incorporated herein by reference in their entireties.

Terahertz (THz) radiation is directed to the desired target, and a reflection or transmission signal is detected and analyzed. The detected signal is a time-dependent signal, and is therefore transformed, e.g., with a Fourier transform, to obtain frequency-dependent spectral information. The THz spectral information can sometimes be used to identify particular chemical compositions. For example, certain explosives have unique spectral characteristics in the THz region that may be amenable to standoff detection.

In *Detection and identification of explosives using terahertz pulsed spectroscopic imaging*, Y. C. Shen et al., Appl. Phys. Lett. 86, 241116 (2005) THz-TDS, hereby incorporated by reference, the authors demonstrate using reflection terahertz measurements detection of the absorption spectrum of a particular explosive (RDX).

In particular, spectroscopic methods using terahertz radiation have several unique properties that provide advantages in certain applications. For example, terahertz radiation is non-ionizing. Also, many materials such as clothing, paper, and the like are substantially transparent at this frequency, while other materials, including plastics and ceramics, are readily visible in terahertz imaging. In particular, many chemicals of interest have a characteristic spectrum at terahertz frequencies that are amenable to detection by spectroscopic means.

However, surface roughness features of a target can cause electromagnetic scattering of terahertz waves that decreases the signal-to-noise of the spectral features. The noise can obscure the desired spectral signatures of chemicals at these frequencies. Electromagnetic waves are scattered when they encounter a rough surface having length scale features that are comparable to the wavelength of the wave. THz waves, having wavelengths on order of hundreds of microns, can also suffer from classical electromagnetic scattering caused by embedded internal void volumes or inhomogeneous granularity of the material. The bandwidth of THz pulses is reduced dramatically upon propagation through pellets of granular material. So far, little progress has been made in eliminating the negative effects of scattering. Y. C. Shen et al. showed that by averaging over 1800 disjoint transmission measurements, the granularity scattering effect can be effectively decreased (*Elimination of scattering effects in spectral measurement of granulated materials using terahertz pulsed spectroscopy*, Shen et al., Appl. Phys. Lett., Vol. 92, pp. 051103-3, 2008). Due to the strong absorption of terahertz radiation in transmission through thick layers of materials, and for other practical considerations, reflection geometries are more suitable for the stand-off discrimination of chemicals, as compared to transmission spectroscopy.

In the reflection mode, however, surface roughness is the dominant source of terahertz scattering. Y. Dikmelik et al. modeled the effects of surface roughness by considering the summation of a large number of elemental reflections with different time delays that correspond to the surface height variations at each element (*Effect of surface roughness on reflection spectra obtained by terahertz time-domain spectroscopy*, Y. Dikmelik et al., Opt. Lett., Vol. 31, pp. 2653-2655, 2006).

There remains a need for improved methods and systems for analyzing THz spectrum information to detect chemical compositions in target samples, and in particular for methods that overcome limitations due to surface scattering effects.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

A method for detecting a chemical in a target includes obtaining a terahertz frequency spectrum of the target, transforming the frequency spectrum into a wavelet frequency domain, and analyzing the wavelet coefficients to detect spectroscopic features that would indicate the presence of a particular chemical species.

In an embodiment a terahertz signal is obtained using reflection spectroscopy, and the signal is converted into frequency space using a discrete Fourier transform. In particular, THz-TDS may be used to obtain the terahertz frequency spectrum.

In an embodiment, the terahertz frequency spectrum is detrended prior to implementing the wavelet transform. In another embodiment, the terahertz frequency spectrum is copied, the copies are manipulated, for example, by translation, rotation, and/or reflection, and the manipulated copies are concatenated to generate a terahertz frequency spectrum having zero trend.

In an embodiment, a plurality of terahertz time-domain spectroscopy (THz-TDS) time-domain signals are obtained, Fourier transformed, and averaged to generate the terahertz frequency spectrum that is to be transformed into wavelet frequency space.

In an embodiment, the wavelet transform comprises a Maximal Overlap Discrete Wavelet Transform (MODWT). In an embodiment, the wavelet transform uses a fundamental mother wavelet comprising a Least Asymmetric Daubechies filter.

A method for detecting a chemical in a target includes using THz-TDS to obtain a time-domain signal characterizing the interaction of a terahertz beam with the target, taking a Fast Fourier Transform of the time-domain signal to extract a corresponding frequency spectrum, transforming the corresponding frequency spectrum using a wavelet transform to generate a corresponding wavelet coefficient, and analyzing the wavelet coefficient to detect the presence of a spectroscopic feature indicating a selected chemical.

In an embodiment the THz-TDS comprises reflection spectroscopy, and the wavelet transform comprises a Maximal Overlap Discrete Wavelet Transform. The wavelet coefficients are analyzed to determine if the target includes a chemical having a predetermined dielectric resonance frequency.

In an embodiment the wavelet transform is not an orthonormal transform.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION

Terahertz spectroscopy as discussed above is a promising method for the detection of particular chemicals in targets, and in particular for applications of stand-off detection. However, it is known that electromagnetic scattering of terahertz waves caused by the surface roughness of a target can significantly reduce the signal-to-noise ratio in the detected absorption spectrum, thereby inhibiting the ability to use the detected spectrum to identify particular chemical compositions in or on the target. For example, in experiments discussed below lactose pellets were formed having differing surface roughness properties. To analyze the effect of surface roughness on terahertz reflection spectroscopy, sample targets were prepared with α-lactose monohydrate chosen as a test material because it exhibits an absorption feature or signatures at 0.54 THz, and has been extensively studied in the literature. Lactose is particularly interesting because its dielectric resonances fall very close to signatures of many chemicals of high interest.

Sample targets composed of 80% α-lactose monohydrate and 20% polyethylene powder of spectroscopic grade were prepared with surface roughness imposed from sheets of sandpapers of differing roughness grades. The polyethylene powder is transparent to THz radiation, and was added to improve bonding and the mechanical strength of the targets. For repeatability, the targets were made by pressing the mixture under approximately a 3000 psi load for approximately three hours, with previously characterized sandpaper placed in the press. The sandpaper was peeled away from the target after pressing, thereby forming a rough surface on the target with roughness features that depend on the grit size of the sandpaper. Relatively smooth targets, formed without using sandpaper, were also made. The targets were then analyzed using THz-TDS spectroscopy.

THz pulses were generated by optical rectification of an 800 nm, approximately 45 fs pulse laser with repetition rate of 1 kHz at an average power of 940 mW in a 1-mm thick ZnTe crystal. Reflection spectra of smooth- and rough-surface lactose targets were measured by taking three reflection measurements from the same spot on the pellet and taking a Fast Fourier Transform (FFT) of each measurement after truncating the echo signal and padding it with zeros in the time domain. The average of the three transformed measurements was taken in the frequency domain and the first derivative (with respect to frequency) was taken.

Figure 1:
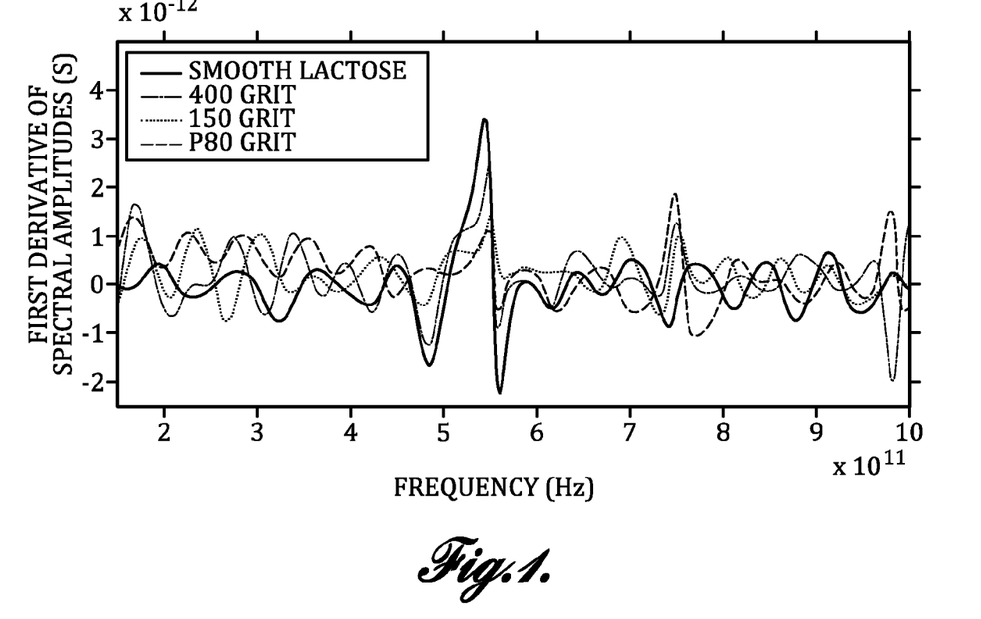
FIG. 1 shows the first derivative of normalized reflection spectral amplitudes obtained using THz-TDS of lactose targets having different surface roughness features.

FIG. 1 shows the first derivative of normalized THz reflection spectral amplitudes (in the range between about 0.1 and 1.0 THz) for reflection data obtained for various lactose targets having surface roughness ranging in increasing order of surface roughness from smooth, to 400 grit, to 150 grit, and P80 grit. The expected resonance frequency of 0.54 THz is clearly apparent for the smooth target (solid line in FIG. 1). However, as the surface roughness of the target increases, the scattering caused by the surface features causes the signal-to-noise of the signal to decrease. At grit sizes of P80 and 150 the reflection spectrum feature at 0.54 THz is buried under the noise level.

In *Application of wavelet transforms in terahertz spectroscopy of rough surface targets*, M. H. Arbab et al., Proc. SPIE 7601, 760106-7 (2010), which is hereby incorporated by reference in its entirety, a wavelet transform method applied to frequency-domain spectrum data was found effective for recovering features in the spectrum, such as the desired dielectric resonance features, to enable the identification of the desired chemical composition. In a later paper, *Retrieval of terahertz spectroscopic signatures in the presence of rough surface scattering using wavelet methods*, M. H. Arbab et al., Appl. Phys. Lett. 97, 181903 (2010), which is hereby incorporated by reference in its entirety, additional aspects of the method are disclosed.

As discussed herein and in the above-referenced papers, a wavelet transform-based method applied to the spectral information in the frequency domain has been found effective in mitigating scattering effects, such that the relevant spectral information may be retrieved to allow for identification of the lactose chemical signature.

Figure 2:
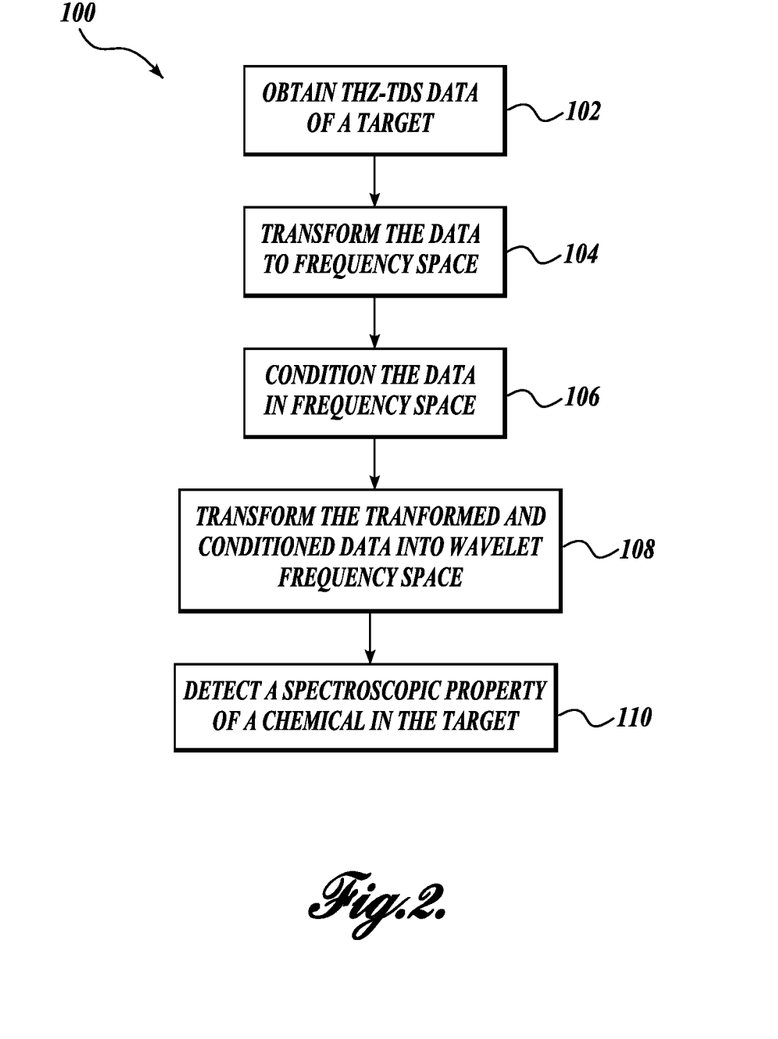
FIG. 2 is a flow chart showing a method for detecting a chemical in a target, in accordance with the present invention.

FIG. 2 illustrates an overview of the method for detecting a chemical in a target in accordance with the present invention. In this exemplary embodiment 100 terahertz spectroscopy data are obtained from the target 102. For example, if THz-TDS is used, short terahertz pulses are generated and interact with the target. It will be appreciated that the THz pulses may contain frequency components over a relatively broad band. For example the frequency components may span the range of 0.05 THz to 4 THz. The electric field of the THz pulse interacts in a detector with a shorter laser pulse to produce an electrical signal proportional to the electric field of the THz pulse. The signal is scanned and its electric field is constructed as a function of time. The data are then transformed to frequency space using a Fourier transform 104. The resulting frequency space signal may then be conditioned 106, for example as discussed below. The conditioning may include normalization, averaging, and/or detrending. The transformed and conditioned signal is then transformed into wavelet frequency space 108. The doubly transformed data are then used to analyze a chemical property of the target 110, e.g., to detect the presence of a particular chemical composition in the target.

In a currently preferred embodiment a Maximal Overlap Discrete Wavelet Transform (MODWT) was used to successfully extract resonance frequency information from the detected terahertz spectrum obtained from a target sample, wherein the surface of the target sample was sufficiently rough to cause significant scatter-induced degradation of the signal-to-noise ratio in the spectroscopic data.

The definitions and nomenclature used for the representation of the wavelet transforms hereafter follows closely that of Percival and Walden (D. Percival and A. Walden, *Wavelet Methods for Time Series Analysis*, Cambridge University Press, Cambridge, 2000), which is hereby incorporated by reference. Methods based on wavelet transforms are well suited for analyzing series having localized features. MODWT, a variation of Discrete Wavelet Transforms, will now be described. Let X represent an N-dimensional vector whose elements, $X_0, X_1, \ldots, X_{N-1}$ with constant sampling interval $\delta$, comprise the real-valued data series to be analyzed. For example, in a particular application of the present method, vector X represents normalized averaged reflection spectral amplitudes of five spatially disjoint THz-TDS measurements of one of the lactose targets described above. For any positive integer $J_0$, the level $J_0$ MODWT of X consists of $J_0+1$ vectors of dimension N, namely, $\tilde{W}_1, \ldots, \tilde{W}_{J_0}$ and $\tilde{V}_{J_0}$, where each $\tilde{W}_j$ vector contains the MODWT wavelet coefficients associated with changes in X on scale $\tau_j \equiv \delta \cdot 2^{j-1}$ and $\tilde{V}_{J_0}$ contains the MODWT scaling coefficients associated with averages on scale $\delta \cdot 2^{J_0}$. These coefficients are defined by $$\tilde{W}_{j,t} \equiv \sum_{l=0}^{L_j-1} \tilde{h}_{j,l} X_{(t-l) \bmod N} \text{ and } \tilde{V}_{j,t} \equiv \sum_{l=0}^{L_j-1} \tilde{g}_{j,l} X_{(t-l) \bmod N},$$

where $t=0, 1, \ldots, N-1$, and $\tilde{h}_{j,l}$ and $\tilde{g}_{j,l}$ are the elements of the $j^{th}$ level MODWT wavelet and scaling filters, respectively, and $L_j \equiv (2^j-1)(L-1)+1$ is the width of the MODWT filters, where L is the width of the fundamental (or 'mother') wavelet filter. In the currently preferred embodiment L=8. The MODWT filters are defined in terms of the $j^{th}$ level DWT equivalent wavelet and scaling filters $h_{j,l}$ and $g_{j,l}$ by $$\tilde{h}_{j,l} = \frac{h_{j,l}}{2^{j/2}} \text{ and } \tilde{g}_{j,l} = \frac{g_{j,l}}{2^{j/2}}.$$

A filter $\{h_l: l=0, 1, \ldots, L-1\}$ of even width L is a wavelet filter if and only if $$\sum_{l=0}^{L-1} h_l = 0 \text{ and } \sum_{l=0}^{L-1} h_l h_{l+2n} = \begin{pmatrix} 0, & \text{if } n \text{ is a non-zero integer} \\ 1, & \text{if } n = 0 \end{pmatrix}.$$

The scaling filter is defined in terms of the wavelet filter by $g_l \equiv (-1)^{l+1} h_{L-1+l}$.

By definition of the MODWT coefficients, we can write:

$$X = \sum_{j=1}^{J_0} \tilde{W}_j^T \tilde{W}_j + \tilde{V}_{J_0}^T \tilde{V}_{J_0} \equiv \sum_{j=1}^{J_0} \tilde{D}_j + \tilde{S}_{J_0},$$

where $\tilde{\mathcal{W}}_j^T$ and $\tilde{\mathcal{V}}_{J_0}^T$ are N×N matrices such that $\tilde{W}_j = \tilde{\mathcal{W}}_j X$ and $\tilde{V}_{J_0} = \tilde{\mathcal{V}}_{J_0} X$. This equation describes the reconstruction of the original data series, X, by performing the inverse of the wavelet transform described above.

In the wavelet literature vocabulary, the above equation for X is commonly referred to as the MODWT Multi Resolution Analysis (MRA) of X, in terms of a "smooth part" vector, $\tilde{S}_{J_0}$ and "details" vector, $\tilde{D}_j$, $j=1, 2, \ldots, J_0$. MRA represents a decomposition of X into a series of vectors that correspond to variations of X on different scales, $\tau_j$, which are integer multiples of the sampling interval.

MODWT is not an orthonormal transform. In order to accommodate a maximal overlap between $X_i$ and the wavelet filters, a circular boundary condition is used. To handle this circular boundary condition, in one embodiment a detrending operation on X is performed before implementation of the MODWT, which is accomplished by subtracting a fitted curve from the original data series. In another embodiment described below, the non-detrended data series is artificially extended, e.g., through translation, mirror, and rotation operations, to define a periodic signal with zero trend. An advantage of MODWT over regular discrete wavelet transforms lies in the insensitivity of the analysis to the starting point on the data series for the placement of the wavelet filter.

If the selected fundamental wavelet filter has a zero-phase function, the wavelet transform coefficients can be readily aligned with the original data series. This allows the frequency of detected features in the wavelet transform coefficients to be directly compared with the original data, e.g., the location of the dielectric resonances.

In the currently preferred embodiment of the method, the Least Asymmetric (LA) Daubechies filter of the eight-order, LA(8), was selected. The LA mother wavelet is a linear-phase filter. In order to compensate for its non-zero phase value, analytical relationships can be derived to give translation factors for the wavelet coefficients at each $j^{th}$ level. Therefore, in effect, a zero-phase wavelet filter can be achieved by advancing the filtering output by a constant shift or translation associated with the $j^{th}$ order. $TW_j$ is used herein to refer to a translated wavelet coefficient related to the $j^{th}$ order.

Figure 3:
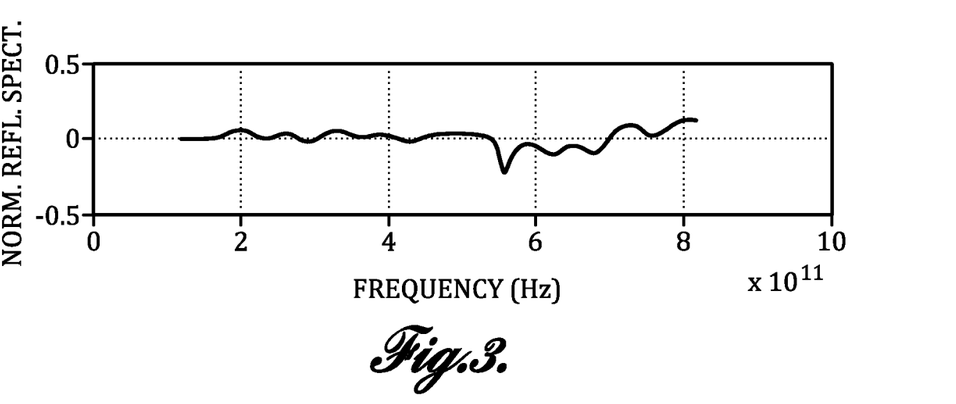
FIG. 3 shows a detrended normalized reflection spectrogram of terahertz measurements averaged over five disjoint locations on a P80 grit rough surface lactose target.
Figure 4A:
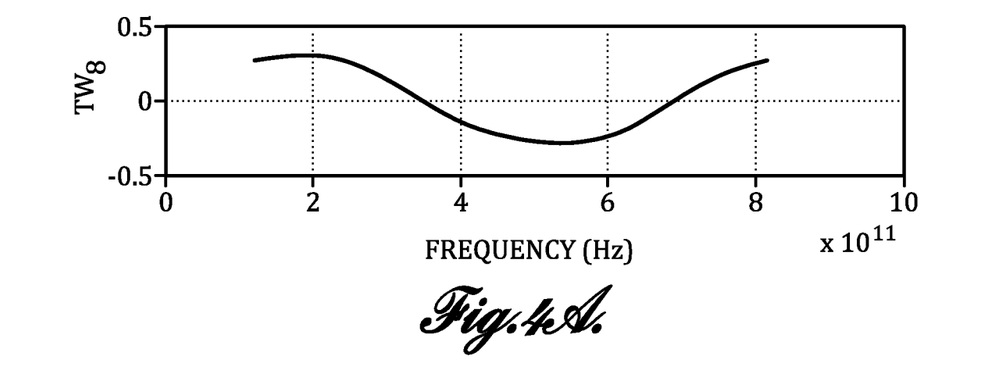
FIGS. 4A-4H show the translated wavelet coefficients for wavelets $TW_8 \ldots TW_1$, respectively, obtained using the method of FIG. 2.
Figure 4B:
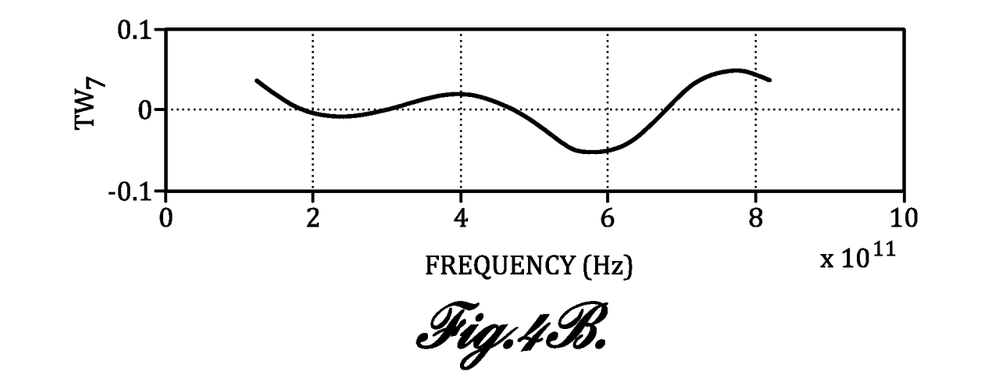
Figure 4C:
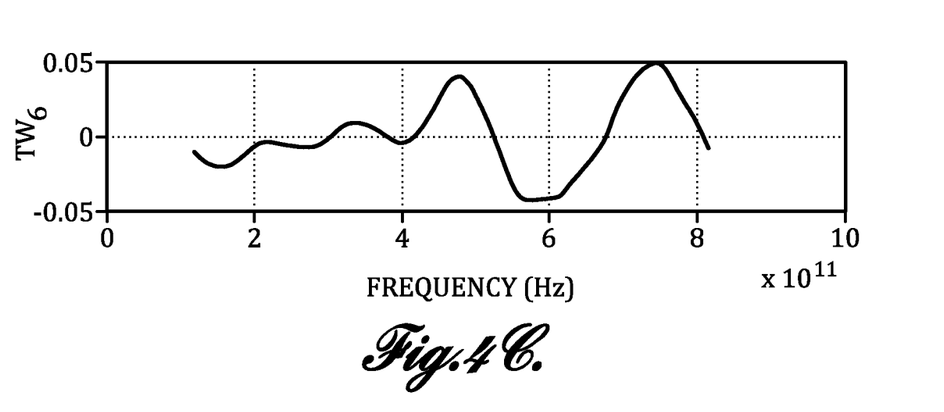
Figure 4D:
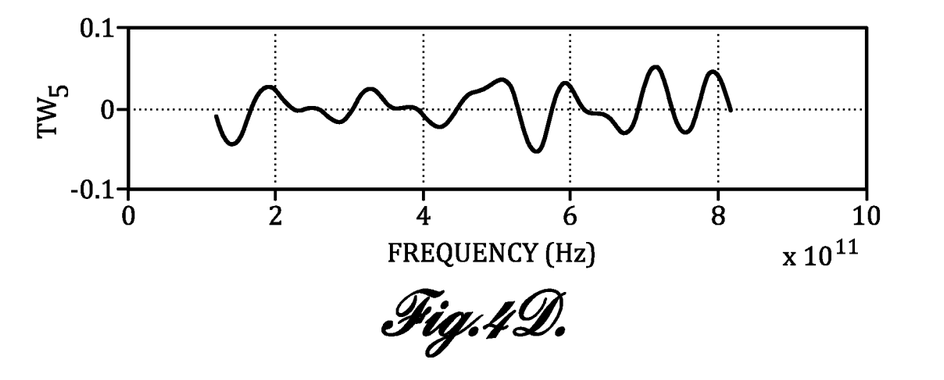
Figure 4E:
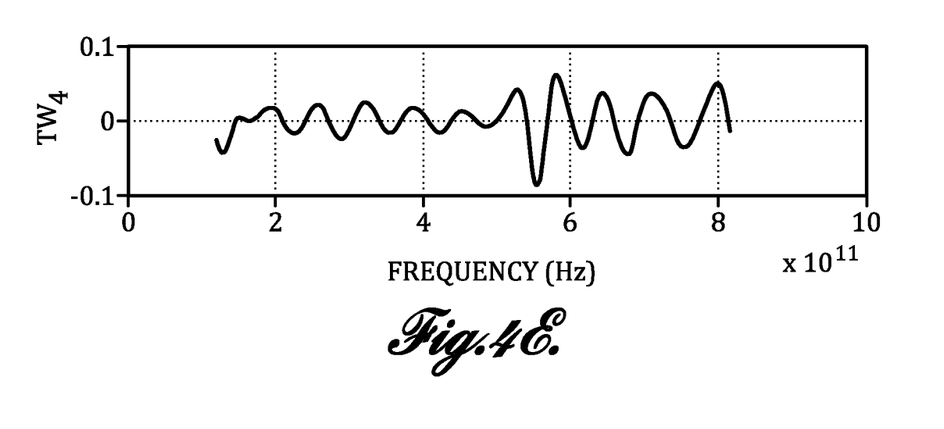
Figure 4F:
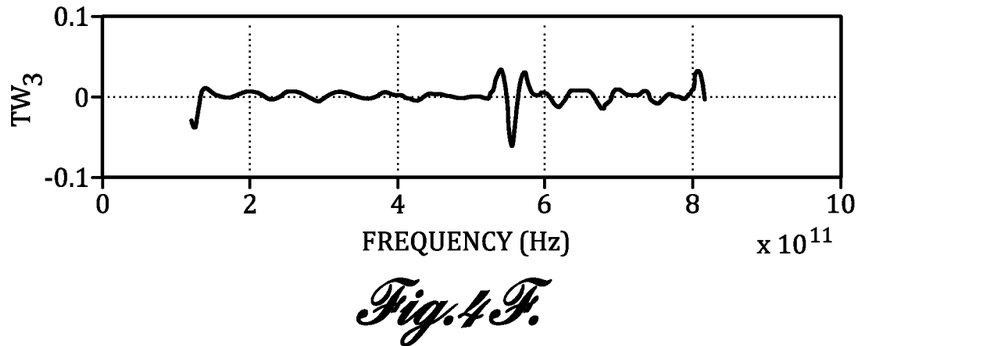
Figure 4G:
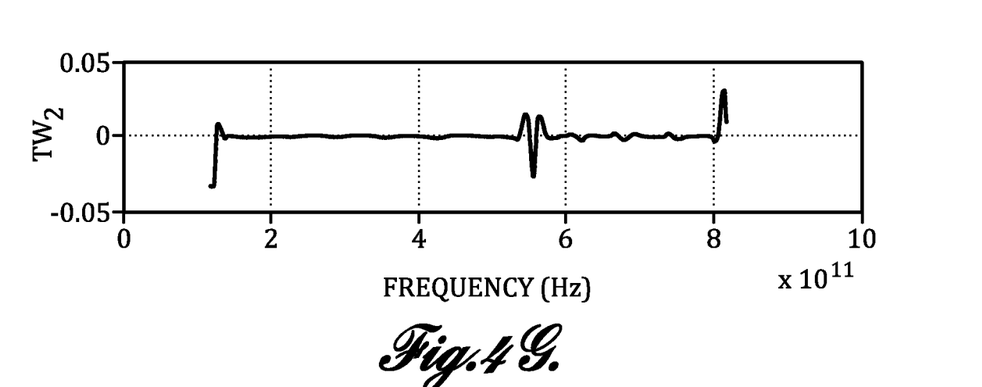
Figure 4H:
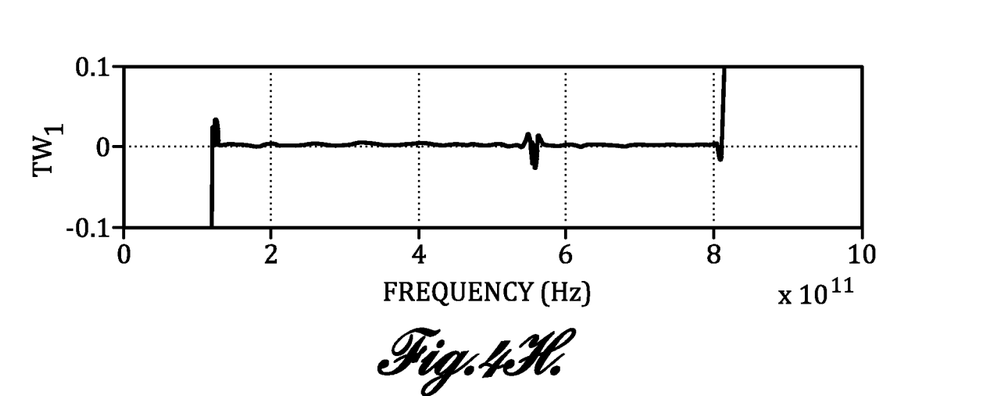

FIG. 3 shows a detrended normalized reflection spectrogram (data series) of the terahertz measurements averaged from five disjoint locations on a P80 grit rough surface lactose target. FIGS. 4A-4H show the corresponding MODWT wavelet coefficients for the data series defined by the reflection spectrum, in accordance with the method described above. Details of the method and results in this implementation are described in more detail in the technical paper incorporated by reference above. In particular, since $J_0=8$, $\tilde{W}_j$ is an 8×N matrix. FIG. 4A plots the wavelet coefficient corresponding to $j=8$ ($TW_8$) after it has been translated according to the zero-phase condition. This wavelet corresponds to the $\tau_j=0.317$ THz scale, and indicates where in the frequency domain variation at this scale is appreciable. Similarly, FIG. 4B plots the wavelet coefficient corresponding to row $j=7$ ($\tau_j=0.16$ THz), FIG. 4C plots the wavelet coefficient corresponding to row $j=6$ ($\tau_j=0.079$ THz), and similarly through FIG. 4H which plots the wavelet coefficient corresponding to row $j=1$ ($\tau_j=0.0025$ THz).

It will be appreciated, in particular from examination of the wavelet coefficients corresponding to j=1, 2, and 3 (FIGS. 4F-4H), that when effects of large frequency scale variations are removed from the original normalized reflection spectrum, the translated wavelet coefficients clearly locate the resonance in the dielectric constant for the target, i.e., in this case the known resonance frequency for lactose. It can be seen that $TW_1$, $TW_2$ and $TW_3$, which represent the variations on some of the finer frequency scales, appear to only respond strongly to the spectral absorption feature. Therefore, the data decomposition and synthesis using MODWT can provide a robust detection method by recognition of spectral transitions of materials and identify their locations on the frequency axis, despite the presence of strong rough surface scattering effects.

Figure 5:
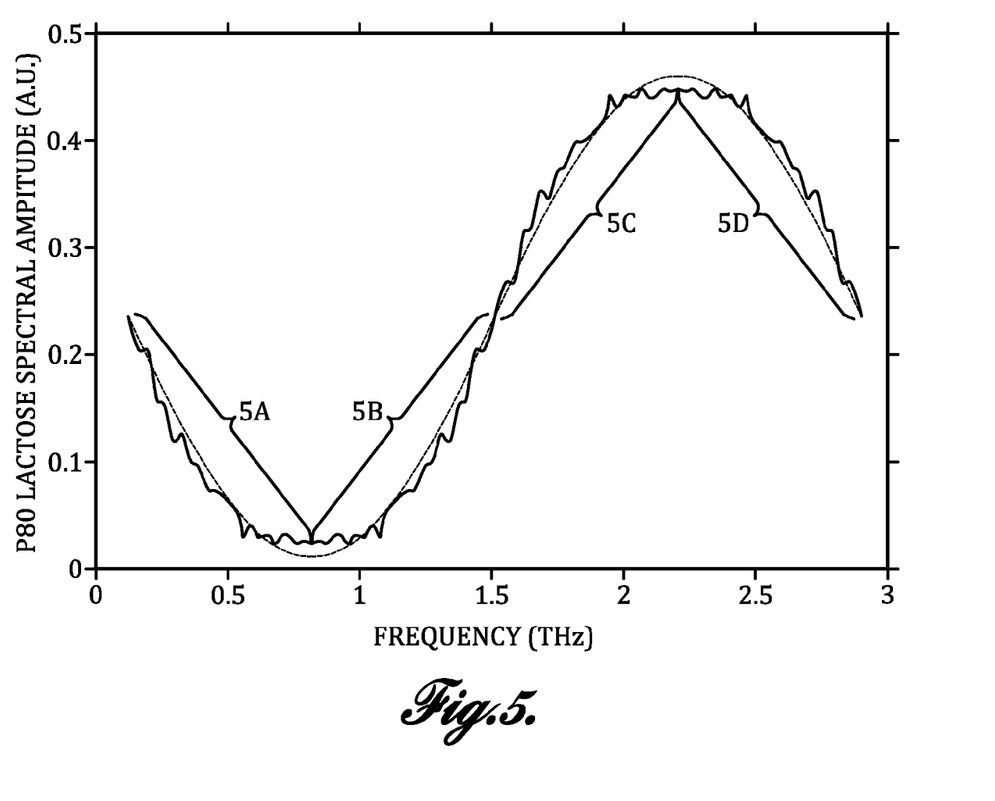
FIG. 5 shows an artificial periodic extension to the data signal that facilitates using the data signal without requiring a detrending step.

Because the Kirchoff approximation, which is often used in modeling scattering, places limitations on the surface roughness of a target, a model-independent detrending method would be beneficial for general application of the present method in an automated stand-off detection system. To address this issue, a periodic extension algorithm is presented to accommodate the circular boundary condition of the MODWT. The original data series (e.g., the non-detrended data series corresponding to FIG. 3) was used to construct the extended series shown in FIG. 5. In this method the periodic extension is constructed using four concatenated copies of the non-detrended data series, wherein the individual copies are manipulated to produce the data series indicated in FIG. 5. For example, the first half of the series may be constructed by mirroring a copy of the original data series about a vertical plane intersecting the last point of the original series. The second half may be constructed by mirroring the first half of the series through a horizontal plane intersecting the first point of the original series and shifting it to the right in FIG. 5 to concatenate with the first half of the extended series. Therefore, by eliminating any discontinuity between $X_0$ and $X_{N-1}$, the circular boundary condition of the MODWT would not require any detrending operation. Following this extension algorithm, an automated detection device can implement the above inverse MODWT analysis without any prior knowledge of the inherent frequency dependence of the THz spectral amplitudes.

Although the example described above used data generated by averaging data obtained from a plurality of points on the target, the present inventor has conducted tests comparing location of the absorption spectrum feature determined using a THz-TDS spectrum obtained from a single point on the target, and repeated the single-point tests multiple times at different locations on the target. The predicted location (frequency) for the spectroscopic feature (e.g., the center peak) was found to be quite consistent, for both smooth and rough targets. The method may therefore be reliably used to identify a particular spectroscopic signature using a single point measurement on the target. This advantage allows for very rapid acquisition of data, and may not require the target be isolated or immobilized for any appreciable period of time. This provides clear advantages in particular for stand-off detection of chemicals in a target.

Although a currently preferred embodiment of the method has been described with reference to overcoming the scatter resulting from surface roughness in reflection spectroscopy data, one of the powers of the wavelet-based detection of chemicals, as disclosed herein, is that it may be readily employed for both reflection and transmission data. In other words, it doesn't matter from what kind of measurement geometry we acquired the X vector. Whether the undesirable noisy data is caused by scattering due to rough surfaces, other sources of noise in the measurement system, volumetric voids or inhomogeneity in the target, or the like, the disclosed wavelet method may be used to isolate the natural spectroscopic feature from other artifacts in the signal and provide a much cleaner and better spectrum to detect chemicals with a higher signal-to-noise ratio.

While illustrative embodiments have been illustrated and described, it will be appreciated that various changes can be made therein without departing from the spirit and scope of the invention.

The invention claimed is:

1. A method for detecting a chemical in a target comprising:
   (a) using terahertz time-domain spectroscopy to measure a time-domain signal and transforming the time-domain signal to a first terahertz frequency spectrum characterizing the interaction of a pulsed terahertz beam with the target;
   (b) transforming the first terahertz frequency spectrum using a wavelet transform in the frequency domain to generate corresponding wavelet coefficients that indicate the presence of particular chemical species;
   (c) analyzing the wavelet coefficients to detect the presence of a selected chemical.

2. The method of claim 1, wherein the first terahertz spectrum is obtained using reflection spectroscopy.

3. The method of claim 1, wherein the time-domain signal is transformed to the first terahertz frequency spectrum by taking a discrete Fourier transform of the time-domain signal.

4. The method of claim 1, further comprising detrending the first terahertz frequency spectrum prior to transforming the first terahertz frequency spectrum, wherein the detrending comprises modifying the first terahertz frequency spectrum to remove any overall slope to accommodate using a circular boundary condition.

5. The method of claim 1, wherein the first terahertz frequency spectrum is obtained using terahertz time-domain spectroscopy to obtain an intermediate time-domain signal, copying the intermediate time-domain signal a plurality of times, and manipulating and concatenating the copies of the intermediate time-domain signal to generate the first terahertz frequency spectrum such that the first terahertz frequency spectrum has zero trend.

6. The method of claim 1, wherein the first terahertz frequency spectrum is obtained using terahertz time-domain spectroscopy to obtain a plurality of time-domain signals, taking a discrete Fourier transform of each of the plurality of time-domain signals to generate a plurality of intermediate frequency space signals, and averaging the plurality of intermediate frequency space signals.

7. The method of claim 6, wherein the plurality of time-domain signals are obtained from different locations on the target.

8. The method of claim 1, wherein the wavelet transform comprises a Maximal Overlap Discrete Wavelet Transform.

9. The method of claim 1, wherein the wavelet transform generates a plurality of wavelet coefficients that are analyzed to determine if the target includes a chemical having a predetermined dielectric resonance frequency.

10. The method of claim 1, wherein the wavelet transform uses a fundamental mother wavelet comprising a Least Asymmetric Daubechies filter.

11. A method for detecting a chemical in a target comprising:
   (a) using terahertz time-domain spectroscopy to obtain a time-domain signal characterizing the interaction of a terahertz beam with the target;

(b) taking a Fast Fourier Transform of the time-domain signal to extract a corresponding frequency spectrum;

(c) transforming the corresponding frequency spectrum using a wavelet transform to generate corresponding wavelet coefficients indicating the presence of particular chemical species;

(d) analyzing the wavelet coefficients to detect the presence of a spectroscopic feature indicating a selected chemical.

12. The method of claim 11, wherein the terahertz time-domain spectroscopy comprises reflection spectroscopy.

13. The method of claim 11, wherein the wavelet transform comprises a Maximal Overlap Discrete Wavelet Transform.

14. The method of claim 11, wherein the wavelet coefficients are analyzed to determine if the target includes a chemical having a predetermined dielectric resonance frequency.

15. The method of claim 11, wherein the wavelet transform is not an orthonormal transform.

16. The method of claim 11, wherein the wavelet transform uses a fundamental mother wavelet comprising a Least Asymmetric Daubechies filter of the eighth order.

17. The method of claim 11, wherein the time-domain signal characterizing the interaction of a terahertz beam with the target is the average of a plurality of spectrogram data obtained from disjoint locations on the target.

18. A method for detecting a chemical in a target comprising:

(a) using terahertz time-domain spectroscopy to measure a time-domain signal and transforming the time-domain signal to a first terahertz frequency spectrum characterizing the interaction of a terahertz beam with the target;

(b) transforming the first terahertz frequency spectrum using a wavelet transform in the frequency domain to generate corresponding wavelet coefficients, wherein the wavelet coefficients indicate the presence of particular chemical species;

(c) analyzing the wavelet coefficients to detect the presence of a selected chemical.

19. The method of claim 18 wherein the terahertz beam comprises a plurality of frequency components.

* * * * *